(12) United States Patent
Ramsey, Jr.

(10) Patent No.: US 11,610,656 B2
(45) Date of Patent: Mar. 21, 2023

(54) CONSUMER MEDICATION ADHERENCE SYSTEM

(71) Applicant: Alvin Lee Ramsey, Jr., Brighton, MA (US)

(72) Inventor: Alvin Lee Ramsey, Jr., Brighton, MA (US)

( * ) Notice: Subject to any disclaimer, the term of this patent is extended or adjusted under 35 U.S.C. 154(b) by 331 days.

(21) Appl. No.: 16/840,545

(22) Filed: Apr. 6, 2020

(65) Prior Publication Data
US 2021/0104308 A1  Apr. 8, 2021

Related U.S. Application Data

(60) Provisional application No. 62/912,094, filed on Oct. 8, 2019.

(51) Int. Cl.
| | |
|---|---|
| *G16H 20/13* | (2018.01) |
| *G16H 40/67* | (2018.01) |
| *G16H 40/20* | (2018.01) |
| *G06Q 10/10* | (2012.01) |
| *G06Q 30/00* | (2012.01) |
| *G06K 7/14* | (2006.01) |
| *G06F 8/65* | (2018.01) |
| *A61J 1/03* | (2006.01) |
| *G06Q 10/109* | (2023.01) |
| *G06Q 30/018* | (2023.01) |
| *H04W 88/02* | (2009.01) |

(52) U.S. Cl.
CPC .............. *G16H 20/13* (2018.01); *A61J 1/03* (2013.01); *G06F 8/65* (2013.01); *G06K 7/1417* (2013.01); *G06Q 10/109* (2013.01); *G06Q 30/0185* (2013.01); *G16H 40/20* (2018.01); *G16H 40/67* (2018.01); *A61J 2205/10* (2013.01); *A61J 2205/30* (2013.01); *H04W 88/02* (2013.01)

(58) Field of Classification Search
CPC ........ G16H 20/13; G16H 40/67; G16H 40/20; G06Q 10/109; G06Q 30/0185; G06F 8/65; A61J 1/03; A61J 2205/30; A61J 2205/10; G06K 7/1417; H04W 88/02
See application file for complete search history.

(56) References Cited

U.S. PATENT DOCUMENTS

| | | | |
|---|---|---|---|
| 10,825,559 B1 * | 11/2020 | Hopen | G06K 7/1417 |
| 11,017,893 B2 * | 5/2021 | Hopen | G16H 40/67 |
| 11,042,738 B2 * | 6/2021 | Stuck | G06K 7/10722 |
| 2014/0188502 A1 * | 7/2014 | Defrank | G16H 40/67 |
| | | | 705/2 |

(Continued)

*Primary Examiner* — Michael Collins
(74) *Attorney, Agent, or Firm* — Bay State IP, LLC

(57) ABSTRACT

A medication adherence system with a pill container with 2D barcodes printed along one or more compartment stores medication to be taken. A user scans the 2D barcode using a first electronic device with a mobile app installed and the user confirms the correct medication for the appropriate day and the system synchronizes scanning and scheduling data to an Internet cloud service. Separately, proxy users and caregivers can use a second electronic device to retrieve data from the cloud and manage a patient's medication scheduling and the devices are in data communication through the mobile app and associated cloud service. Proxy users can seamlessly monitor and manage medication adherence of semi-independent persons using the described system.

4 Claims, 10 Drawing Sheets

(56) References Cited

U.S. PATENT DOCUMENTS

| | | | |
|---|---|---|---|
| 2016/0120759 A1* | 5/2016 | Chen | A61J 7/0481 |
| | | | 340/573.1 |
| 2017/0087059 A1* | 3/2017 | Rodriguez | A61J 7/0427 |
| 2018/0113993 A1* | 4/2018 | Wiser | A61J 7/0436 |
| 2021/0001061 A1* | 1/2021 | Calderon Oliveras | |
| | | | A61M 15/0065 |
| 2021/0065863 A1* | 3/2021 | Hopen | G16H 80/00 |

\* cited by examiner

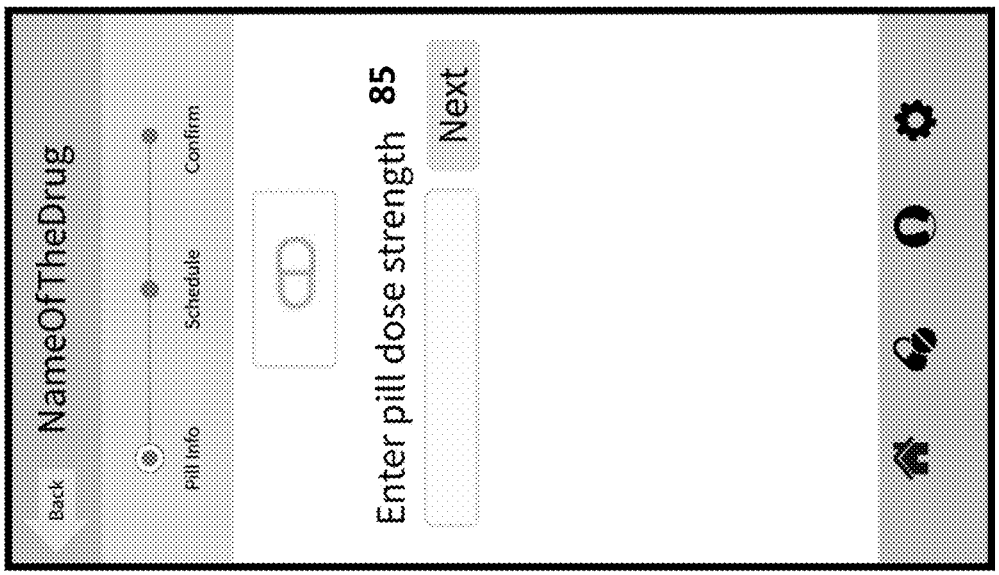
FIG. 8
FIG. 9
FIG. 10
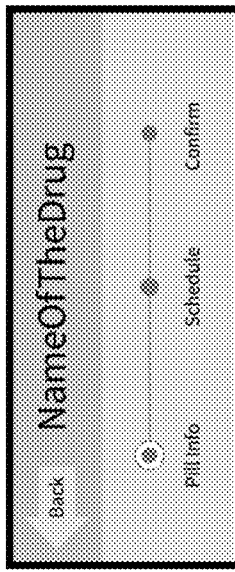
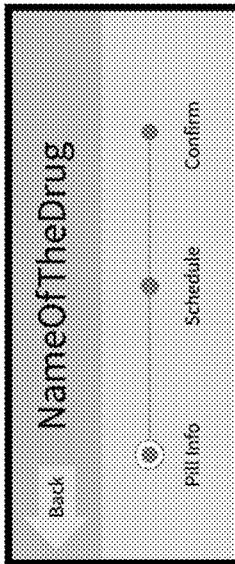

CONSUMER MEDICATION ADHERENCE SYSTEM

CROSS REFERENCE TO RELATED APPLICATION

This application claims the benefit of and takes priority from U.S. Provisional Patent Application Ser. No. 62/912,094 filed on Oct. 8, 2019, the contents of which are herein incorporated by reference.

BACKGROUND OF THE INVENTION

Field of the Invention

The instant system generally relates to medication management and compliance, and more particularly to a system and method for electronically tracking individual compliance of taking medication by a $3^{rd}$ party through a mobile application.

DESCRIPTION OF THE ART

Several systems have been developed over the years to assist with the management of medication. One of the earlier methods, involved the first bar code scanning system for medication adherence which was developed by the Veterans Health Administration in 1995 for inpatient care[1,2]. The emphasis was on verifying the "5 R's"—namely, the right medication, the right dose, the right patient, the right time, and the right route. Bar codes were associated with the medication packages to confirm the medication, dosage, and route type (e.g., orally, or intravenous). The patient would also typically have a bar coded tag around the wrist, and the nurse administering the medication would also have a bar code scanner connected to a mobile computer in order to scan the patient and the medication, and the computer that captures the bar code scans would record the time.

[1] Johnson, Connie L., et al. "Using BCMA software to improve patient safety in Veterans Administration Medical Centers." Journal of healthcare information management: JHIM 16.1 (2002): 46-51.

[2] Patterson, Emily S., Richard I. Cook, and Marta L. Render. "Improving patient safety by identifying side effects from introducing bar coding in medication administration." Journal of the American Medical Informatics Association 9.5 (2002): 540-553.

Additionally, there have been numerous patents that cover methods and products that utilizes bar codes as part of a medication management system. The bar codes are primarily used to identify either the drug in the container, which patient the drug is for, or the specific pharmacy order associated with the drug. However, none of the patents describe the use of bar code scanning to explicitly determine if scheduled pills were removed from its individual dose storage container. Such a method would significantly streamline the process of electronically capturing medication adherence information.

SUMMARY OF THE INVENTION

The instant system, method and accompanying series of apparatuses, as illustrated herein, are clearly not anticipated, rendered obvious, or even present in any of the prior art mechanisms, either alone or in any combination thereof. A versatile system and method for medication adherence and real-time verification of the adherence by a $3^{rd}$ party.

A primary object of the instant system is to track medication compliance by utilizing a pill box with time intervals with a two-dimensional barcode associated with each interval.

Another object of the instant system is to provide a device that is able to scan the barcode associated with each time interval in order to verify if and when the medication with the specific time interval has been taken by the user.

Another object of the instant system is to provide a device that would be able to record whether the medication has been taken by the user based on whether the scan of the barcode was successful or if the scan failed.

Another object of the instant system is to track the success of the scan of the barcode as a set of electronic data for medication compliance.

Another object of the instant system is to confirm the correct medication for the appropriate day, and to have the system synchronize scanning and scheduling data to an Internet cloud service where caregivers may use a second electronic device to retrieve data from the cloud and manage the user's medication scheduling.

There has thus been outlined, rather broadly, the more important features of the medication adherence system in order that the detailed description thereof that follows may be better understood, and in order that the present contribution to the art may be better appreciated. There are additional features of the system that will be described hereinafter and which will form the subject matter of the claims appended hereto.

In this respect, before explaining at least one embodiment of the system in detail, it is to be understood that the system is not limited in its application to the details of construction and to the arrangements of the components set forth in the following description or illustrated in the drawings. The system is capable of other embodiments and of being practiced and carried out in various ways. Also, it is to be understood that the phraseology and terminology employed herein are for the purpose of description and should not be regarded as limiting.

These together with other objects of the system, along with the various features of novelty, which characterize the system, are pointed out with particularity in the claims annexed to and forming a part of this disclosure. For a better understanding of the system, its operating advantages and the specific objects attained by its uses, reference should be made to the accompanying drawings and descriptive matter in which there are illustrated preferred embodiments of the system.

BRIEF DESCRIPTION OF THE DRAWINGS

Figures 11, 12:
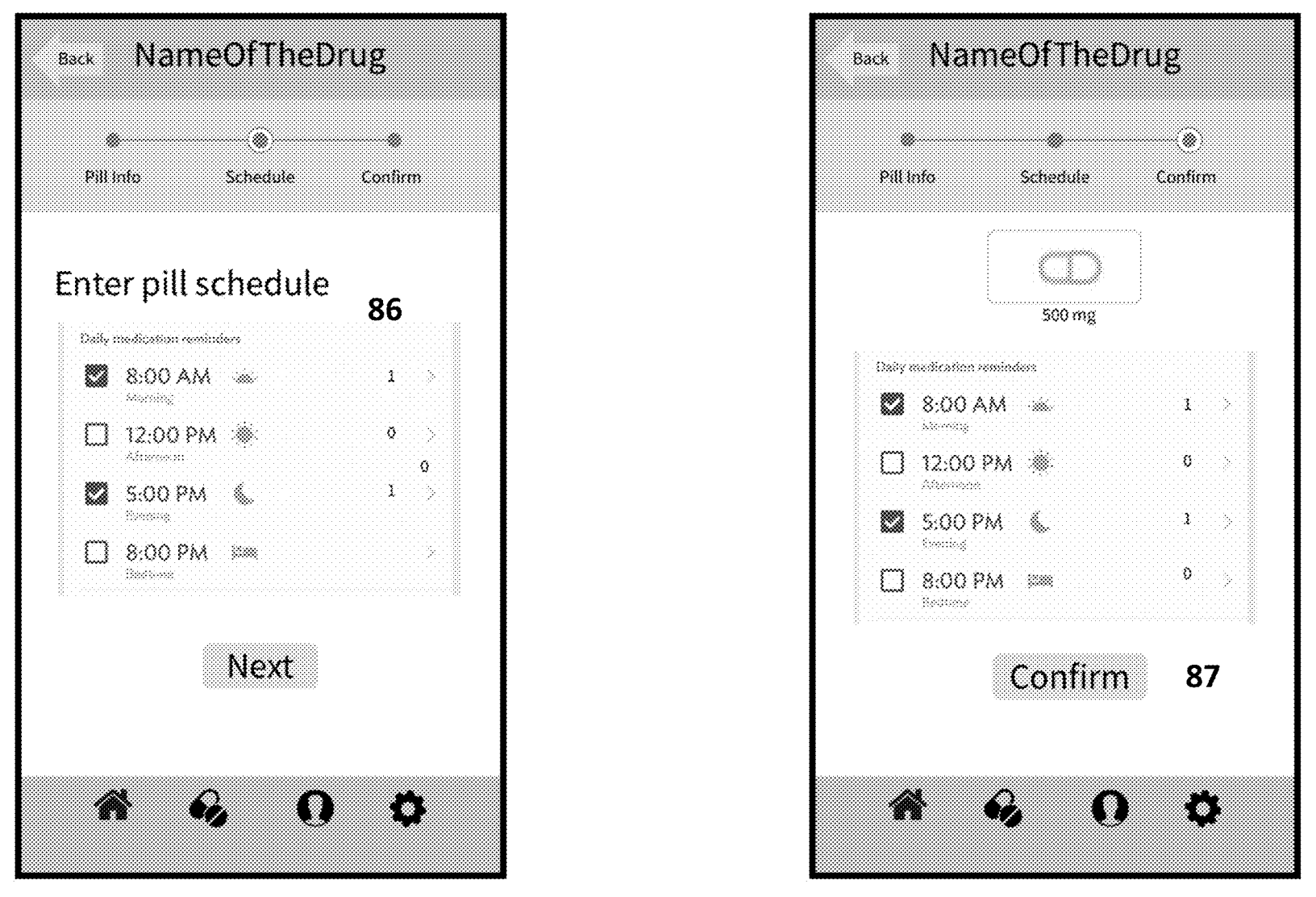

FIGS. 8-12 illustrate the application method to add a schedule of medications and other pills to be taken on each day or a particular day.

DETAILED DESCRIPTION OF THE SEVERAL EMBODIMENTS

The detailed description set forth below in connection with the appended drawings is intended as a description of presently preferred embodiments of the system and does not represent the only forms in which the present system may be constructed and/or utilized. The description sets forth the functions and the sequence of steps for constructing and operating the system in connection with the illustrated embodiments.

The following description particularly relates to a consumer medication adherence system using a unique pill container, a first electronic device with a mobile application, a second electronic device in data communication with the first device, and an internet cloud service where medical adherence data can be stored and shared with caregivers. The device and associated method function to assist in monitoring medication compliance and decrease the rate of medication non-adherence among consumers by providing a standardized system for managing all a patient's medications simultaneously.

Figure 1:
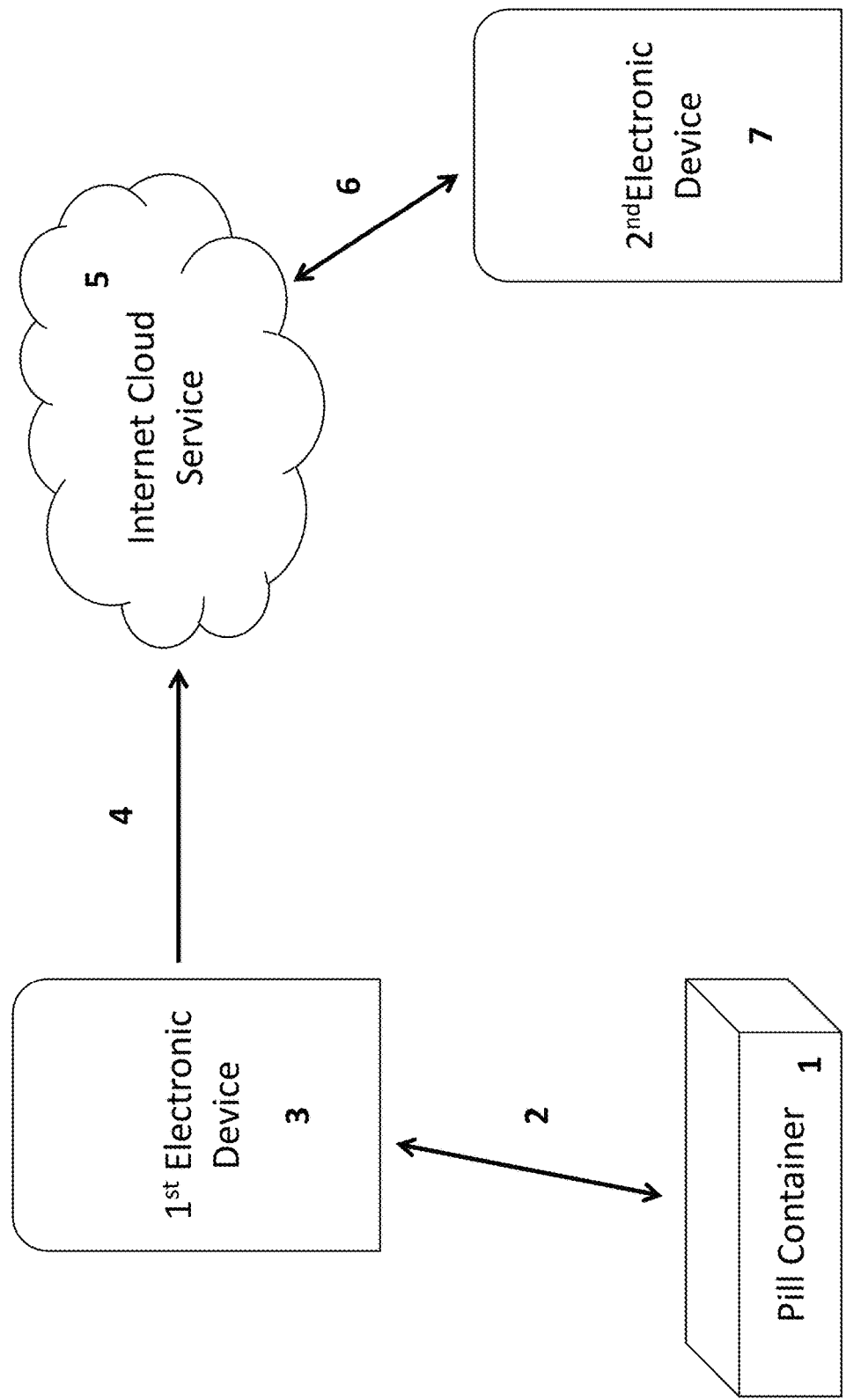
FIG. 1 illustrates a system diagram of the medication adherence system.

FIG. 1 illustrates an overview of the medication adherence system. A pill container 1 with 2D barcodes printed along one or more compartment stores medication to be taken. At step 2 a user scans the 2D barcode using a first electronic device 3 with the mobile app installed. At step 4 the user confirms the correct medication for the appropriate day and the system synchronizes scanning and scheduling data to an Internet cloud service 5. Proxy users and caregivers can use a second electronic device 7 to retrieve data from the cloud and manage a patient's medication scheduling at step 6. The devices are in data communication through the mobile app and associated cloud service. Proxy users can seamlessly monitor and manage medication adherence of semi-independent persons using the described system.

Figure 2:
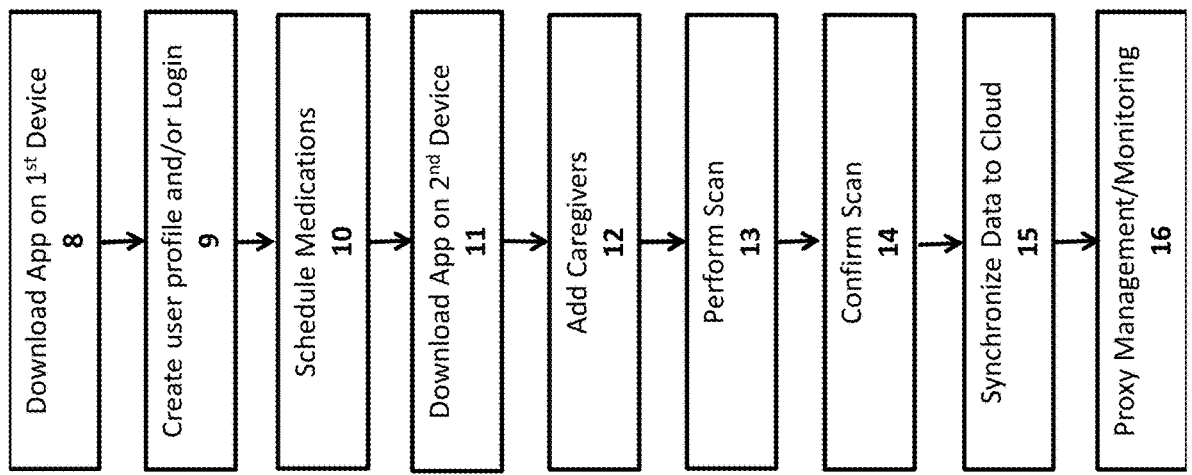
FIG. 2 illustrates a flow diagram for utilizing a mobile application in connection with the medication adherence system.
Figure 3:
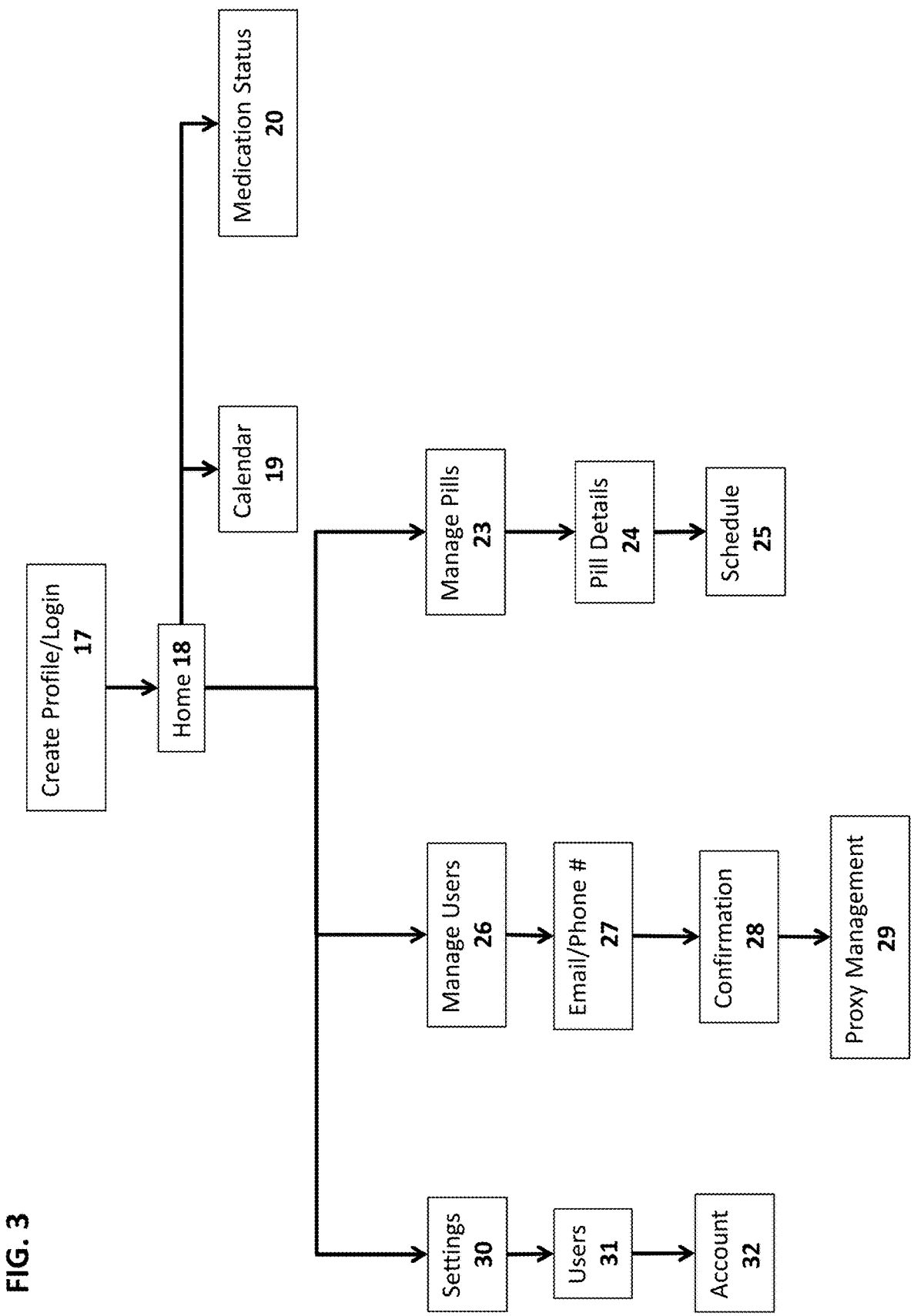
FIG. 3 illustrates a flow diagram for utilizing the medication adherence system via the mobile application.
Figure 7:
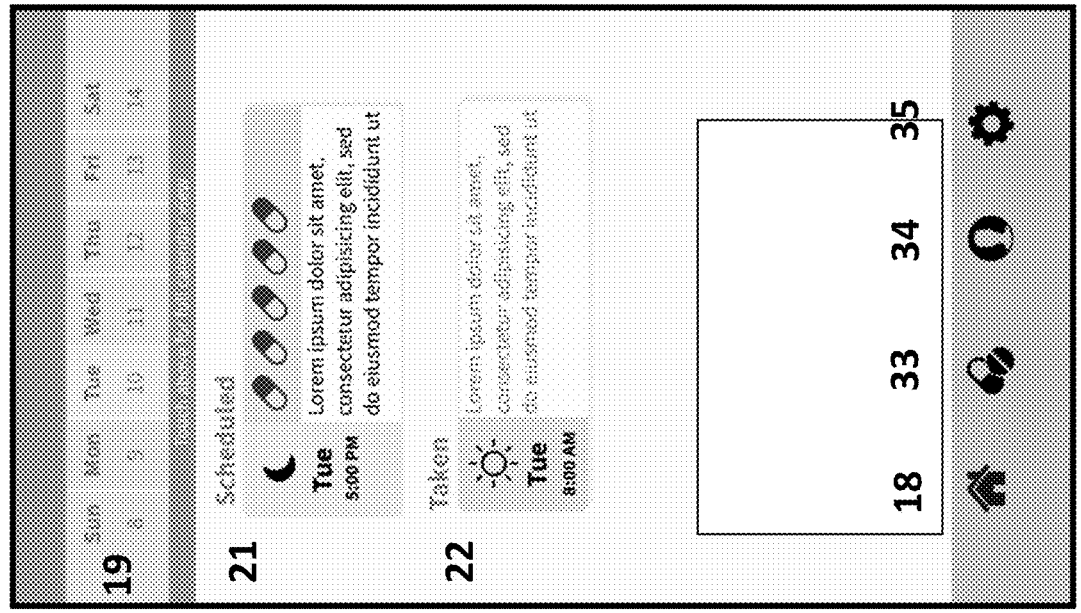
FIG. 7 illustrates an embodiment for a mobile application installed on a first electronic device possessed by a user/patient.

FIGS. 2 & 7 illustrates an embodiment for a mobile application installed on a first electronic device possessed by a user/patient. The application manages a patient's medication schedule, reminds a patient when to take their medication, and sends notifications to caregivers for monitoring a patients medication adherence information. A patient may download 8 the mobile app through the iTunes or Google Play mobile app stores onto a mobile device preferably including a camera capable of scanning 2D barcodes and maintaining the time at which a scan was taken. After successful download, a user is prompted to enter their name, email, mobile phone number, and a password to register with the network and create an account 9. The patient can then schedule medications and other pills to be taken 10. Proxy users must also download the mobile app to a second electronic device 11 through the same process described above. Once a user and proxy user/caregiver have downloaded the mobile app to the first and second electronic devices, the user can add a caregiver 12 to their personal network. The system can alert the patient at the scheduled time to take a particular day's medication to perform a scan 13. The user confirms the correct medication has been scanned for the correct day 14 and the mobile app synchronizes the adherence data 15 to an Internet Cloud Service. Users and caregivers can monitor and manage medication adherence and scheduling data 16 that has been synchronized to the cloud through mobile app on each electronic device.

After successfully creating new user profile or logging in 17, the first page to appear is the home screen FIG. 7. A user will see medication status 20 for that day under "Scheduled" 21 and pills already taken under "Taken" 22. A weekly calendar 19 is displayed along the top of the home screen with the current day highlighted upon opening the mobile app. The patient can use the calendar to view a pill schedule for an upcoming day of the week or view previous days of the week to confirm pills taken. A user can expand the week calendar into a full month view by selecting a day of the week other than the current day. A menu along the bottom of the screen allows a user to return to the home screen 18, manage pills 23 with the pill icon 33, manage users 26 with the person icon 34, and change any settings within the mobile app 30 with the gear icon 35. From the Manage Pills tab, a user enters details 24 regarding their medication and creates a schedule 25 to manage and notify the user when to take medication. From the Manage Users tab, a user adds caregivers by inputting their email or phone number 27. Both parties then confirm that the caregiver has been added to the network 28. From the account screen, a user can manage permissions and add additional non-patient caregivers as remote managers of the pill regiment. Remote caregivers can be added and identified by either email or mobile phone number.

In order to view or manage the patient's medication scheduling and adherence, the remote caregiver will also download the app and create a user profile. Once a new caregiver profile is created, the system will recognize the relationship between the caregiver and patient. A proxy user could then view and manage a patient's medication adherence and scheduling. The settings tab 30 allows a user to change any account settings 32 or any settings related to connected proxy users 31.

Figure 4:
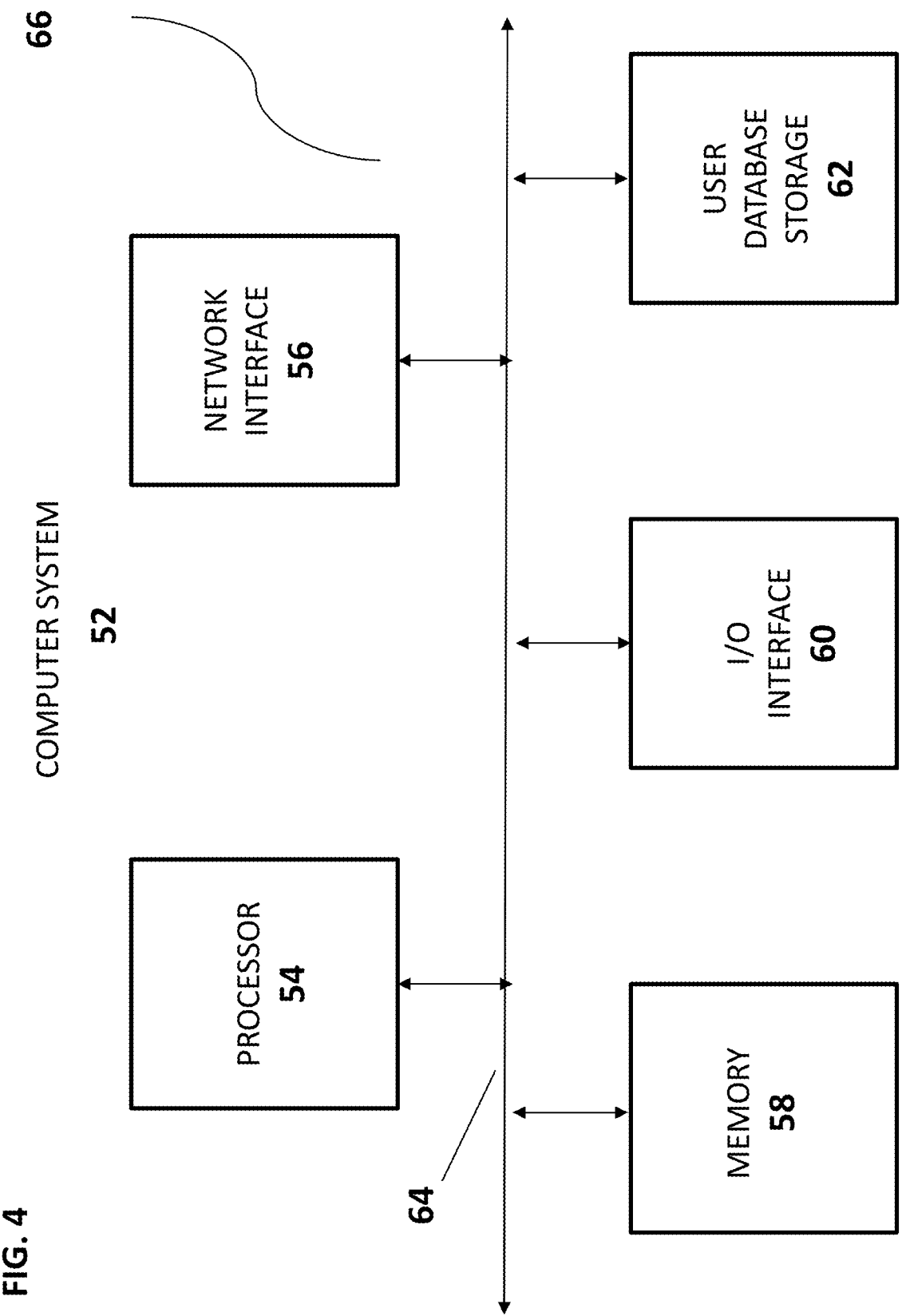
FIG. 4 illustrates one embodiment of an exemplary computing system, wherein the systems and methods disclosed herein may be implemented using one or more computer systems.

FIG. 4 illustrates an exemplary embodiment of a computer system 52, wherein the systems and methods disclosed herein may be implemented using one or more computer systems. As shown, the computer system 52 can include one or more processors 54 which can control the operation of the computer system 52. The processor(s) 54 can include any type of microprocessor or central processing unit (CPU), including programmable general-purpose or special-purpose microprocessors and/or any one of a variety of proprietary or commercially available single or multi-processor systems.

The computer system 52 can also include one or more memories 58, which can provide temporary storage for code to be executed by the processor(s) 54 or for data acquired from one or more users, storage devices, and/or databases. The memory 58 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies. The various elements of the computer system 52 can be coupled to a bus system 64. The bus system can be any one or more separate physical busses, communication lines/interfaces, and/or multi-drop or point-to-point connections, connected by appropriate bridges, adapters, and/or controllers. The computer system 52 can also include one or more network interface(s) 56, one or more input/output (IC)) interface(s) 60, and one or more storage device(s) 62. The network interface(s) 56 can enable the computer system 52 to communicate with remote devices 66 (e.g., other computer systems) over a network, and can be, for example, remote desktop connection interfaces, Ethernet adapters, and/or other local area network (LAN) adapters. The IO interface(s) 60 can include one or more interface components to connect the computer system 52 with other electronic equipment.

For example, the IO interface(s) 60 can include high speed data ports, such as USB ports. Additionally, the computer system 52 can be accessible to a human user, and thus the IO interface(s) 60 can include displays, speakers, keyboards, pointing devices, and/or various other video, audio, or alphanumeric interfaces. The storage device(s) 62 can include any conventional medium for storing data in a non-volatile and/or non-transient manner. The storage device(s) 62 can thus hold data and/or 5 instructions in a persistent state (i.e., the value is retained despite interruption of power to the computer system 52). The storage device(s) 62 can include one or more hard disk drives, flash drives, USB drives, optical drives, various media cards, and/or any combination thereof and can be directly connected to the computer system 52 or remotely connected thereto, such as over a network.

In addition, not all of the illustrated elements need to be located on or in the same physical or logical machine. Rather, the illustrated elements can be distributed in nature, e.g., using a server farm or cloud-based technology. Exemplary computer systems include conventional personal electronic devices, minicomputers, tablet computers, PDAs, mobile phones, and the like. Although an exemplary computer system is depicted and described herein, it will be appreciated that this is for sake of generality and convenience. In other embodiments, the computer system may differ in architecture and operation from that shown and described here.

Figure 5:
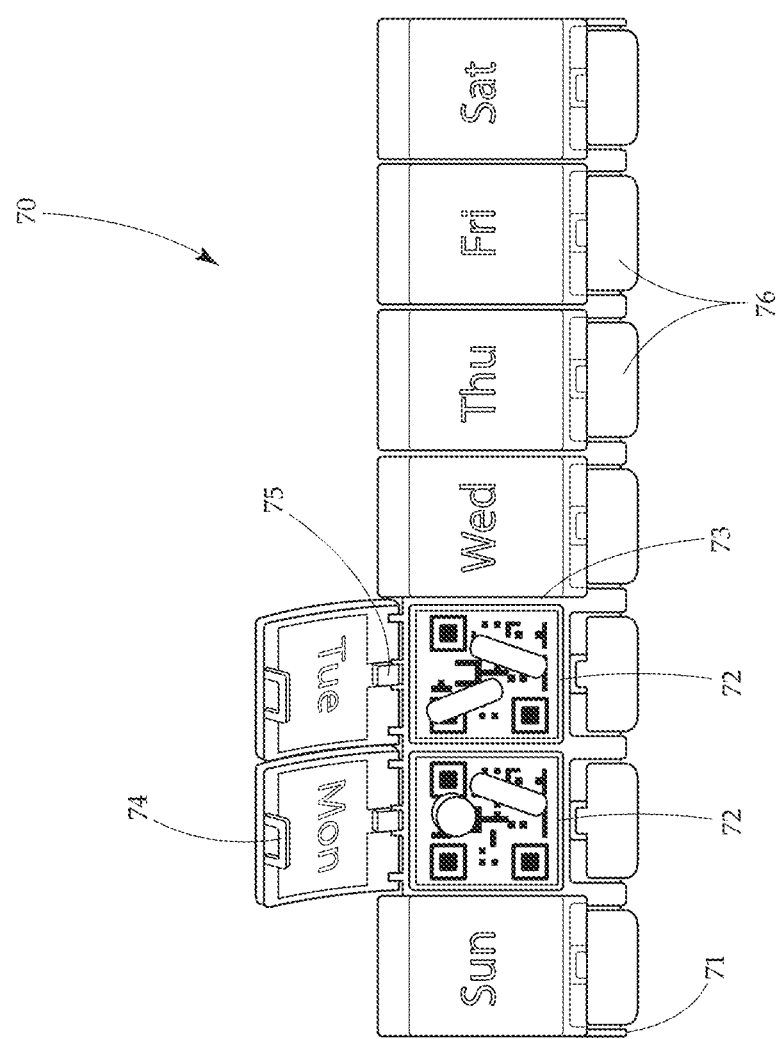
FIG. 5 illustrates an embodiment of a pill container in the form of a pillbox comprising a housing.

FIG. 5 illustrates an embodiment of a pill container in the form of a pillbox 70 comprising a housing 71 separated into several individual compartments 72 by partition 73. Each compartment 72 comprises four walls, a floor, and a lid 74 covering an opening at the top of each compartment. The lid 74 is movably attached to the housing by an attaching means, such as a hinge assembly 75. The lid and/or housing may also include one or more opening elements. Release buttons 76 may be placed along one side of the housing corresponding to each compartment that open the compartment when pressed.

Alternatively, a groove may be disposed along the edge of the lid to assist lifting the lid to access the interior of a compartment. The lid is constructed of transparent or semi-transparent plastic and allows clear viewing of the compartment contents by a user. In one embodiment, the housing is separated into 7 compartments arranged to hold one week of medication. Abbreviations for each day of the week may be printed on the lids to assist a user in selecting the correct medication for the correct day. In alternate embodiments, the pillbox can be arranged with 14 or as many as 30 compartments for two week or month long medication scheduling.

Figure 6:
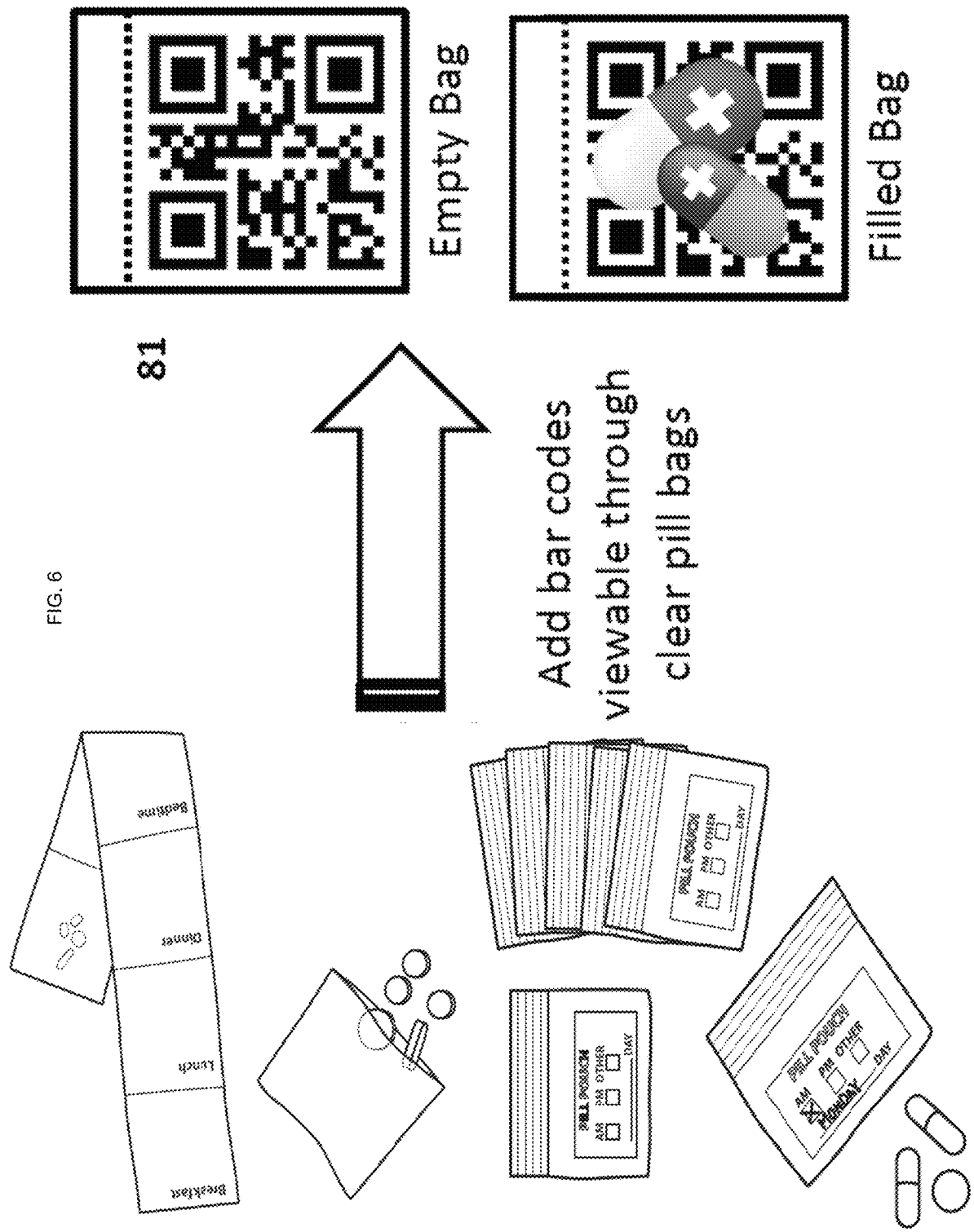
FIG. 6 illustrates a further alternate embodiment where the pill container comprises a pill bag.

FIG. 6 illustrates a further alternate embodiment where the pill container comprises a pill bag 77. The pill bag 77 constructed of clear plastic comprises a sealable closure 78, material around the seal that can be removed to open the seal for single use or remain attached for re-sealable use 79, a label with identifying information 80, and a 2D barcode printed on a white background 81. The bag may be disposable for single use such as the ones automatically filled by strip packaging machines, or may be re-sealable which would be filled manually and allow it to be used again. The plastic bags can be scanned in the same manner as the pillbox. The 2D barcode 81 can either be printed onto the bag itself or stuck onto the bag as a sticker.

The important part of the 2D barcode 81 is that it is clearly viewable by the user and by the user's mobile electronic device. The label displaying identifying information 80 regarding the contents and scheduled day for the bag is disposed in such a way to maintain clear viewing of the 2D barcode 81 through the bag. The print or sticker should show the 2D barcode on one side and a label for medication information on the other side. The side with the 2D barcode should be facing into the bag, i.e. the 2D barcode is placed on one wall of the bag so it can be viewed by looking through the clear plastic of the other wall. Once a user identifies the appropriate bag for the appropriate day, the user removes the pills from the bag and scans the 2D barcode, described in more detail below.

The 2D barcode 81, also known as a matrix barcode, printed on the bottom of each compartment or pill bag to identify and monitor medication usage. Two-dimensional matrix barcodes such as QR codes have a square structure with square rectangles at several corners. The 2D barcode further assists in visual identification of occupied compartments as pills occupying a compartment obscure the barcode, thus making it easier for a user to identify and select the correct medication from the correct compartment. The housing, partition, and floor are formed of white plastic while the barcode is printed along the floor of each compartment in legible ink. The contrasting colors and complex pattern formed by the barcode over a white background on the floor of each compartment are visually relevant. Positioning the barcode on the floor of each compartment and on the back wall of the pill bag creates a distinct background against which pills in an occupied compartment can be clearly seen by a user. The design is particularly useful among populations frequently prescribed multiple medications, such as the elderly. A patient with poor eyesight or motor skills will more easily and quickly be able to locate the appropriate medication assigned to the appropriate day using the present invention compared to what currently exists in the art.

FIGS. 8-12 illustrate the application method to add a schedule of medications and other pills to be taken on each day or a particular day. In one embodiment, the system is configured to work with once-per-day medication schedules. Meaning a user would store seven days of medication to be taken once per day in a pillbox containing seven compartments. Alternatively, the pillbox can be configured to accommodate medication schedules including multiple doses per day. For example, the pillbox may contain fourteen compartments to accommodate a twice-a-day medication schedule per week. The patient can choose a time for the app to expect the pills to be scanned or set the schedule according to a regular once-per-day interval. These times can be configured and altered to accommodate any schedule. Once the patient's medication schedule is set, the app expects a scan from the appropriate compartment to be scanned on the appropriate day.

In order to schedule medication, a user selects the pill icon from the home screen to open the pill management screen. The user then inputs the name of the drug on the first screen FIG. 8. After typing in the name of the drug 82, the user selects "Next" to continue adding more information. The subsequent screen FIG. 9 prompts the user to select the shape 83 and color 84 of the medication. Again the user selects "Next" to continue the scheduling process. On the next screen FIG. 10, the user enters the strength of the medication per dose 85. Again the user selects "Next" to continue the scheduling process. Times during the day for a user to take the medication can be selected from the Schedule screen FIG. 11. Users can select up to four times a day to schedule pills: morning (default 8:00 am), mid-day (default 12:00 pm), evening (default 5:00 pm) and night (default 8:00 pm). At a scheduled time, the system begins a 1-hour window to accept the scan and will expect a scan of the compartment associated with the proper day. Again, up to four time slots 86 can be selected in a given day for a medication schedule. The user selects "Next" one last time to reach a confirmation screen FIG. 12. After reviewing all the displayed information a user confirms the scheduling of the medication by selecting "Confirm" 87. Medication scheduling data is stored on a user's first mobile device and is synchronized to an Internet cloud service. The app will now be expecting a scan of the 2D barcode for the compartment associated with the same day and time for the medications scheduled under this process.

Figure 14:
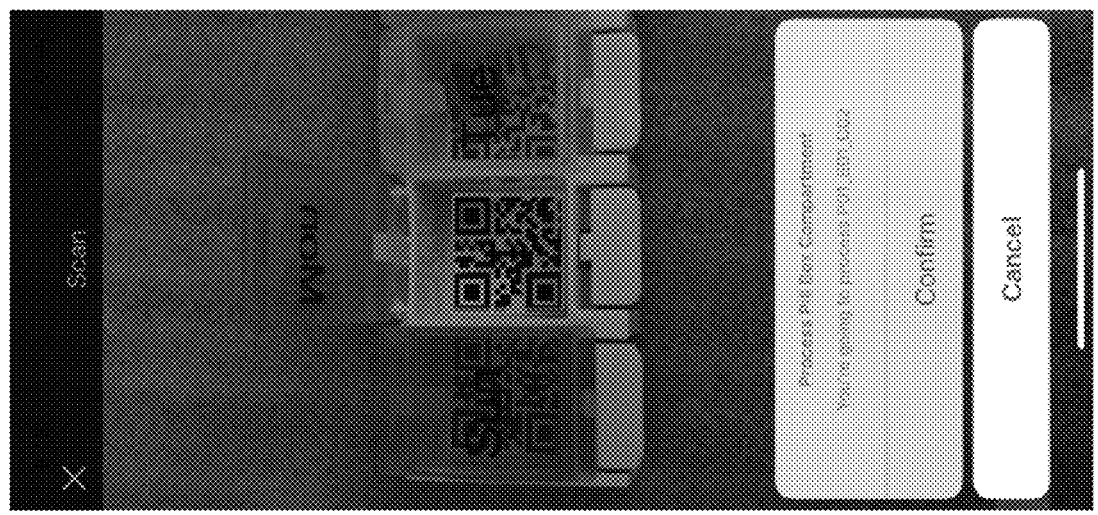
FIGS. 13 & 14 illustrate a first mobile device performing scans of the pillbox under varying circumstances.
Figure 13:

FIGS. 13 & 14 illustrate a first mobile device performing scans of the pillbox under varying circumstances. The unique 2D barcode 81 printed on the bottom of each compartment particularly identifies each individual compartment in relation to the circumstances under which it is scanned (e.g. the date and time at which the compartment is scanned). When scanned, the application will recognize what compartment and day of the week is associated with the 2D barcode. To perform a successful scan FIG. 13, the scan must be made on the correct day for the appropriate corresponding compartment labeled with the abbreviation for that day. In FIG. 14 for example, if on a Sunday a user selects a compartment labeled for Monday and attempts to scan the barcode contained within, the application will return a message to the user that the scan was not completed successfully. A scan will also fail if the user attempts to complete a scan before removing all the pills from a compartment. The patient will identify the appropriate day by referencing the labeled compartments and ensuring the pills within the compartment match the scheduled medications the mobile app expects to be scanned for that day. The camera of the first electronic device must be able to clearly capture an image of the 2D barcode to extract any data. Therefore, prior to capturing an image of the 2D barcode, the user must remove the pills in the container, which are also obstructing or obscuring the barcode. Ideally, this assumes the user actually takes the medication at the time it is removed from the pill container. Once the scan has been completed, the system synchronizes successful or unsuccessful adherence data to the cloud and all connected proxy users in the patient's network.

What is claimed is:

1. A method for verifying medication compliance configured for use with an apparatus that contains a set of pills comprising the steps of:

employing an apparatus with at least one time interval with a barcode associated with each time interval;

scanning the barcode associated with each time interval to verify if the medication with the time interval has been taken by a user;

utilizing a first mobile device to configure and confirm the medication for the appropriate time interval;

utilizing the first mobile device to synchronize data to an internet cloud service;

utilizing the first mobile device to retrieve data on the internet cloud service; and utilizing a medication compliance system, wherein the system comprises:

a housing separated into a plurality of compartments by partition;

a lid covering an opening at the top of each compartment;

at least one release button placed along the side of the housing associated with each compartment;

a groove disposed along the edge of the lid to assist lifting the lid;

wherein a barcode is printed on the floor inside each compartment;

wherein an abbreviation corresponding with a time interval is printed on the lid to assist a user in selecting the correct medication for the correct time interval;

wherein the lid is movably attached to the housing by an attaching means.

2. The method for verifying medication compliance of claim 1 further comprising the steps of:

synchronizing and managing a user's medication schedule via a mobile application;

reminding the user via the mobile application when to take their medication; and sending notifications to a third party via the mobile application for monitoring and managing the user's medication adherence information.

3. The method for verifying medication compliance of claim 1 further comprising the step of:

downloading and installing the mobile application on a first mobile device.

4. The method for verifying medication compliance of claim 1 comprising the step of:

downloading and installing the mobile application on a second mobile device for data communication with the first device via the mobile application.

* * * * *